US010675005B2

(12) United States Patent
Viggen

(10) Patent No.: US 10,675,005 B2
(45) Date of Patent: Jun. 9, 2020

(54) METHOD AND SYSTEM FOR SYNCHRONIZING CALIPER MEASUREMENTS IN A MULTI-FRAME TWO DIMENSIONAL IMAGE AND A MOTION MODE IMAGE

(71) Applicant: General Electric Company, Schenectady, NY (US)

(72) Inventor: Kjetil Viggen, Trondheim (NO)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 38 days.

(21) Appl. No.: 16/053,421

(22) Filed: Aug. 2, 2018

(65) Prior Publication Data
US 2020/0037997 A1  Feb. 6, 2020

(51) Int. Cl.
| A61B 8/08 | (2006.01) |
| G06T 7/73 | (2017.01) |
| A61B 8/14 | (2006.01) |
| A61B 8/00 | (2006.01) |

(52) U.S. Cl.
CPC .......... *A61B 8/5223* (2013.01); *A61B 8/0883* (2013.01); *A61B 8/14* (2013.01); *A61B 8/463* (2013.01); *A61B 8/469* (2013.01); *G06T 7/73* (2017.01); *G06T 2207/10132* (2013.01); *G06T 2207/20081* (2013.01); *G06T 2207/20084* (2013.01)

(58) Field of Classification Search
None
See application file for complete search history.

(56) References Cited

U.S. PATENT DOCUMENTS

| 8,816,959 B2 | 8/2014 | Pan et al. |
| 2010/0198068 A1 | 8/2010 | Rivaz et al. |
| 2010/0232665 A1* | 9/2010 | Amir ..................... A61B 8/08 382/131 |

(Continued)

FOREIGN PATENT DOCUMENTS

JP  2006-305358 A  11/2006

OTHER PUBLICATIONS

PCT Notification of Transmittal of the International Search Report and the Written Opinion of the International Searching Authority, or the Declaration, dated Oct. 31, 2019 (9 pages).

*Primary Examiner* — Yi Wang
(74) *Attorney, Agent, or Firm* — McAndrews, Held & Malloy, Ltd.; Jacob Groethe; David Bates

(57) ABSTRACT

A system and method for synchronizing caliper measurements in a multi-frame 2D image and an anatomical M-mode image is provided. The method may include selecting a frame of a multi-frame 2D image of a region of interest. The method may include positioning a first caliper measurement on the selected frame. The method may include generating an anatomical M-mode image based on a direction of the first caliper measurement. The method may include automatically overlaying a second caliper measurement on the anatomical M-mode image, the second caliper measurement corresponding with the first caliper measurement on the selected frame. The method may include presenting the selected frame having the first caliper measurement simultaneously with the anatomical motion mode image having the second caliper measurement at a display system.

20 Claims, 7 Drawing Sheets

(56) References Cited

U.S. PATENT DOCUMENTS

| | | | |
|---|---|---|---|
| 2014/0088423 A1* | 3/2014 | Noguchi | A61B 8/0891 |
| | | | 600/440 |
| 2015/0150440 A1 | 6/2015 | Salvati et al. | |
| 2017/0090571 A1 | 3/2017 | Bjaerum et al. | |
| 2017/0124770 A1 | 5/2017 | Vats | |
| 2019/0148011 A1* | 5/2019 | Rao | G16H 50/20 |
| | | | 600/437 |

* cited by examiner

METHOD AND SYSTEM FOR SYNCHRONIZING CALIPER MEASUREMENTS IN A MULTI-FRAME TWO DIMENSIONAL IMAGE AND A MOTION MODE IMAGE

FIELD

Certain embodiments relate to ultrasound imaging. More specifically, certain embodiments relate to a method and system for providing caliper measurements in a multi-frame two-dimensional (2D) image and a motion mode (M-mode) image. The caliper measurement provided in one of the 2D image or M-mode image is synchronized to simultaneously display the measurement in the corresponding M-mode image or 2D image in substantially real-time. The caliper measurement may be provided manually by a user and/or selected caliper measurements may be performed automatically by image detection techniques such as machine learning algorithms (e.g., deep neural networks).

BACKGROUND

Ultrasound imaging is a medical imaging technique for imaging organs and soft tissues in a human body. Ultrasound imaging uses real time, non-invasive high frequency sound waves to produce a two-dimensional (2D) image and/or a three-dimensional (3D) image.

Cardiac measurements are a valuable tool in assessing heart function. Multi-frame 2D ultrasound images and M-mode ultrasound images may be used to obtain measurements of an imaged heart. The cardiac measurements are typically performed manually using one of two processes. A first conventional process includes a user stepping or scrolling through the frames of the multi-frame 2D image to locate an image frame at the correct cardiac phase, typically end systole or end diastole. Once the frame of the multi-frame 2D image is identified, the user may manually position a 2D caliper by selecting start and end points of a two point 2D caliper measurement on anatomical landmark points in the selected 2D image frame. The caliper measurement on the 2D frame provides access to two spatial dimensions, but no temporal information. The lack of temporal information may make it difficult to place the calipers correctly when image quality is not optimal. It may also be difficult to determine from the 2D image whether the measurement is performed in the correct frame. Accordingly, a user may need to scroll back and forth to locate the correct frame by watching the movement of the tissue and valves.

A second conventional process for performing cardiac measurements includes using M-mode images, which provides access to one spatial dimension and time. Often, the direction a user wants to measure may not be aligned with one acquisition beam in the multi-frame 2D image. In these cases, an anatomical M-mode line is placed in the 2D image and an anatomical M-mode image is reconstructed based on the positioning of the anatomical M-mode line. The process of positioning the anatomical M-mode line and subsequently placing the caliper in the anatomical M-mode image can be time consuming, particularly if a user is measuring several dimensions in the same 2D image, along different directions.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for synchronizing caliper measurements in a multi-frame 2D image and an M-mode image, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
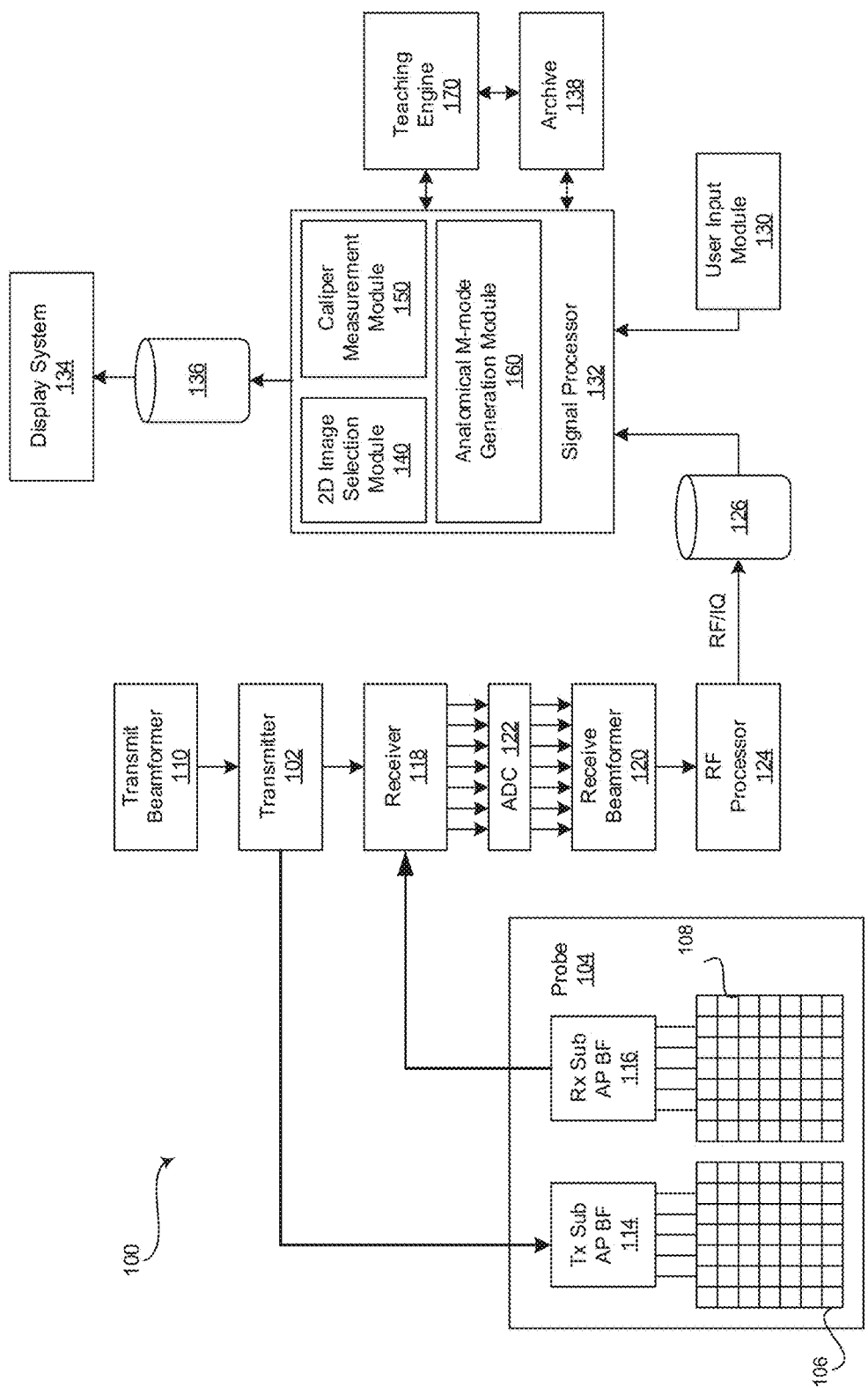
FIG. 1 is a block diagram of an exemplary ultrasound system that is operable to synchronize caliper measurements in a multi-frame 2D image and an M-mode image, in accordance with various embodiments.

Certain embodiments may be found in a method and system for synchronizing caliper measurements in a multi-frame 2D image and an M-mode image. Various embodiments have the technical effect of providing enhanced visualization of caliper measurements. Moreover, certain embodiments have the technical effect of providing accurate caliper placement by using information from both two spatial dimensions and the temporal dimension simultaneously. Furthermore, various embodiments have the technical effect of providing automatic synchronization of 2D and M-mode displays to help a user understand how the data in the 2D and M-mode displays are connected in space and time. Aspects of the present disclosure have the technical effect of providing automated caliper measurements by automatically selecting the frame and anatomical landmark points using machine learning algorithms, such as deep neural networks.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, and/or sub-modes of B-mode and/or CF such as Shear Wave Elasticity Imaging (SWEI), TVI, Angio, B-flow, BMI, BMI_Angio, and in some cases also MM, CM, PW, TVD, CW where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system 100 that is operable to synchronize caliper measurements in a multi-frame 2D image and an M-mode image, in accordance with various embodiments. Referring to FIG. 1, there is shown an ultrasound system 100. The ultrasound system 100 comprises a transmitter 102, an ultrasound probe 104, a transmit beamformer 110, a receiver 118, a receive beamformer 120, a RF processor 124, a RF/IQ buffer 126, a user input module 130, a signal processor 132, an image buffer 136, a display system 134, an archive 138, and a teaching engine 170.

The transmitter 102 may comprise suitable logic, circuitry, interfaces and/or code that may be operable to drive an ultrasound probe 104. The ultrasound probe 104 may comprise a two dimensional (2D) array of piezoelectric elements. The ultrasound probe 104 may comprise a group of transmit transducer elements 106 and a group of receive transducer elements 108, that normally constitute the same elements. In certain embodiment, the ultrasound probe 104 may be operable to acquire ultrasound image data covering at least a substantial portion of an organ, such as the heart or any suitable organ.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive and demodulate the signals from the receive sub-aperture beamformer 116. The demodulated analog signals may be communicated to one or more of the plurality of A/D converters 122.

The plurality of A/D converters 122 may comprise suitable logic, circuitry, interfaces and/or code that may be operable to convert the demodulated analog signals from the receiver 118 to corresponding digital signals. The plurality of A/D converters 122 are disposed between the receiver 118 and the receive beamformer 120. Notwithstanding, the disclosure is not limited in this regard. Accordingly, in some embodiments, the plurality of A/D converters 122 may be integrated within the receiver 118.

The receive beamformer 120 may comprise suitable logic, circuitry, interfaces and/or code that may be operable to perform digital beamforming processing to, for example, sum the delayed channel signals received from the plurality of A/D converters 122 and output a beam summed signal. The resulting processed information may be converted back to corresponding RF signals. The corresponding output RF signals that are output from the receive beamformer 120 may be communicated to the RF processor 124. In accordance with some embodiments, the receiver 118, the plurality of A/D converters 122, and the beamformer 120 may be integrated into a single beamformer, which may be digital.

The RF processor 124 may comprise suitable logic, circuitry, interfaces and/or code that may be operable to demodulate the RF signals. In accordance with an embodiment, the RF processor 124 may comprise a complex demodulator (not shown) that is operable to demodulate the RF signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The user input module 130 may be utilized to input caliper start and end points, caliper measurement selections, patient data, scan parameters, settings, select protocols and/or templates, identify landmarks in ultrasound image data, and the like. In an exemplary embodiment, the user input module 130 may be operable to configure, manage and/or control operation of one or more components and/or modules in the ultrasound system 100. In this regard, the user input module 130 may be operable to configure, manage and/or control operation of the transmitter 102, the ultrasound probe 104, the transmit beamformer 110, the position sensing system 112, the receiver 118, the receive beamformer 120, the RF processor 124, the RF/IQ buffer 126, the user input module 130, the signal processor 132, the image buffer 136, the display system 134, the archive 138, and/or the teaching engine 170. The user input module 130 may include button(s), rotary encoder(s), a touchscreen, motion tracking, voice recognition, a mousing device, keyboard, camera and/or any other device capable of receiving a user directive. In certain embodiments, one or more of the user input modules 130 may be integrated into other components, such as the display system 134, for example. As an example, user input module 130 may include a touchscreen display. In various embodiments, a frame of a multi-frame 2D image may be selected in response to a directive received via the user input module 130. In certain embodiments, one or more caliper measurements may be selected in response to a directive received via the user input module 130. In a representative embodiment, the start and end points of a caliper measurement may be selected in response to a directive received via the user input module 130.

The signal processor 132 may comprise suitable logic, circuitry, interfaces and/or code that may be operable to process ultrasound scan data (i.e., RF signal data or IQ data pairs) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform compounding, motion tracking, and/or speckle tracking. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information. In the exemplary embodiment, the signal processor 132 may comprise a 2D image selection module 140, a caliper measurement module 150, and an anatomical M-mode generation module 160.

The ultrasound system 100 may be operable to continuously acquire ultrasound scan data at a frame rate that is suitable for the imaging situation in question. Typical frame rates range from 20-70 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

Figure 3:
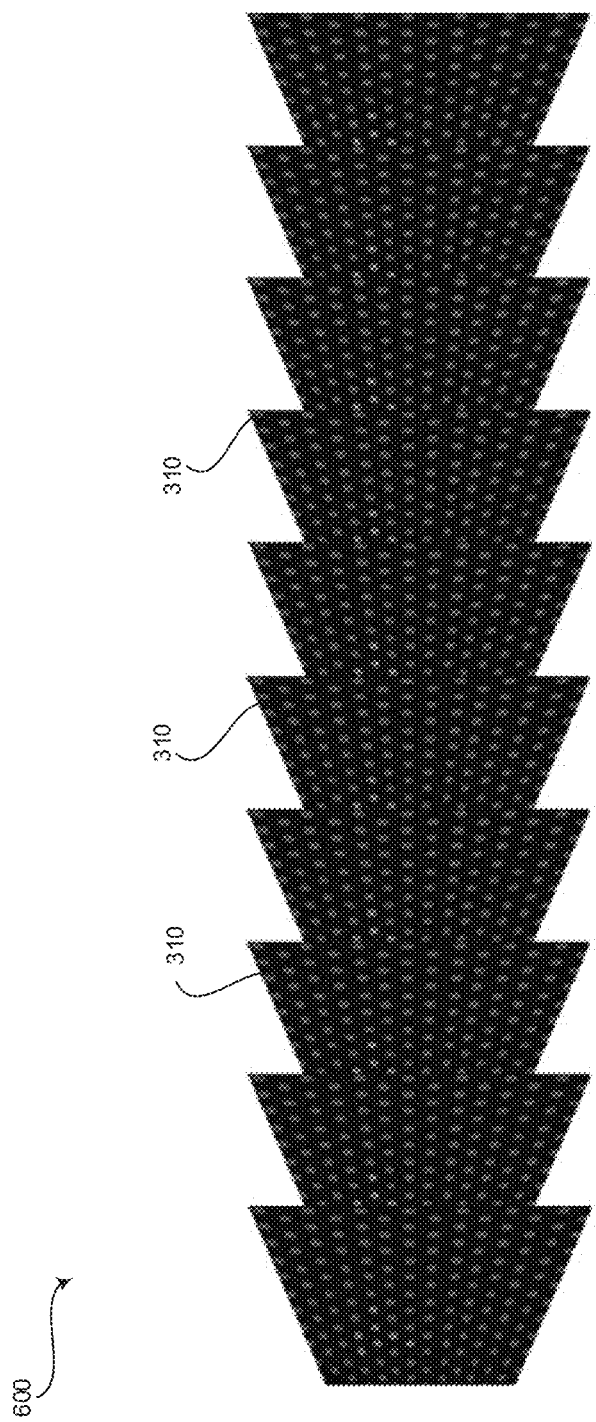
FIG. 3 illustrates an exemplary multi-frame 2D image, in accordance with various embodiments.

The signal processor 132 may include a 2D image selection module 140 that comprises suitable logic, circuitry, interfaces and/or code that may be operable to select a frame of a multi-frame 2D ultrasound image. FIG. 3 illustrates an exemplary multi-frame 2D image 600, in accordance with various embodiments. Referring to FIG. 3, the multi-frame 2D image 600 comprises a plurality of 2D frames 310. Referring again to FIG. 1, a user may provide a selected frame 310 to the 2D image selection module 140 via the user input module 130. In various embodiments, a rotary encoder or other user input module 130 may be rotated or otherwise activated to navigate the frames 310 of the multi-frame 2D image 600. Once the appropriate frame 310 is identified, the user may select the identified frame 310 via the user input module 130 and the selection may be provided to the 2D image selection module 140. The frame 310 of the multi-frame 2D image 600 selected by the user via the 2D image selection module 140 is provided by the selection module 140 to the caliper measurement module 150.

As another example, a user may select one or more caliper measurements to be performed. The 2D image selection module 140 may automatically identify a 2D frame 310 in the multi-frame 2D image 600 based on the one or more measurement selections. Examples of various heart measurements may include, among other things, a left ventricle internal diameter at end systole (LVIDs) measurement, an interventricular septum at end systole (IVSs) measurement, a left ventricle posterior wall at end systole (LVPWs) measurement, and an aortic valve diameter (AV Diam) measurement. In an exemplary embodiment, if a LVIDs measurement is selected, the 2D image selection module 140 may perform a course estimation of end systolic frame time by using detected heart cycle start and end points and applying a heuristic formula for estimating the time of a cardiac phase. The frame 310 of the multi-frame 2D image 600 selected automatically via the 2D image selection module 140 is provided by the selection module 140 to the caliper measurement module 150.

The signal processor 132 may include a caliper measurement module 150 that comprises suitable logic, circuitry, interfaces and/or code that may be operable to position a caliper corresponding to a measurement on the 2D frame 310 provided by the 2D image selection module 140. For example, a user may identify start and end points for a caliper measurement in the 2D frame 310 via the user input module 130. In various embodiments, a mousing device or any suitable user input module 130 may be used to select anatomical landmark points in the selected 2D image frame 310. A line connecting the selected anatomical landmark points may be overlaid by the caliper measurement module 150 on the 2D image frame 310 and a measurement corresponding with the distance between the points may be presented by the caliper measurement module 150 at the display system 134 with the 2D frame 310. The caliper measurement module 150 may store the caliper measurements in archive 138 or any suitable data storage medium. The measurement executed via the caliper measurement module 150 is provided by the measurement module 150 to the anatomical M-mode generation module 160.

As another example, the caliper measurement module 150 may automatically position a caliper corresponding to a measurement on the identified 2D frame 310 by processing the 2D frame 310 to locate anatomical landmark points for the caliper end points based on the selected measurement. In various embodiments, the caliper measurement module 150 includes image detection algorithms, one or more deep neural networks and/or may utilize any suitable form of image detection techniques or machine learning processing functionality configured to automatically identify landmarks in the ultrasound image data. For example, the caliper measurement module 150 may be made up of an input layer, an output layer, and one or more hidden layers in between the input and output layers. Each of the layers may be made up of a plurality of processing nodes that may be referred to as neurons. For example, the input layer may have a neuron for each pixel or a group of pixels from the ultrasound images of the organ. The output layer may have a neuron corresponding to each structure and/or anatomical landmark points within the structure of the organ being imaged. As an example, if imaging a heart, the output layer may include neurons for a pericardium, posterior wall, septal wall, interventricular septum, aortic valve, left ventricle, unknown, and/or other, among other things. Each neuron of each layer may perform a processing function and pass the processed ultrasound image information to one of a plurality of neurons of a downstream layer for further processing. As an example, neurons of a first layer may learn to recognize edges of structure in the ultrasound image data. The neurons of a second layer may learn to recognize shapes based on the detected edges from the first layer. The neurons of a third layer may learn positions of the recognized shapes in the ultrasound image data. The processing performed by the caliper measurement module 150 deep neural network may identify anatomical landmark points with a high degree of probability. The caliper measurement module 150 may overlay a line connecting the anatomical landmark points corresponding with a selected measurement on the 2D image frame 310 and a measurement corresponding with the distance between the points may be presented by the caliper measurement module 150 at the display system 134 with the 2D frame 310. The caliper measurement module 150 may store the caliper measurements in archive 138 and/or at any suitable data storage medium. The measurement automatically performed via the caliper measurement module 150 is provided by the measurement module 150 to the anatomical M-mode generation module 160.

The signal processor 132 may include an anatomical M-mode generation module 160 that comprises suitable logic, circuitry, interfaces and/or code that may be operable to generate an anatomical M-mode image based on the direction of the caliper measurement in the 2D frame 310, overlay the caliper measurement on the M-mode image, and display the M-mode image with overlaid caliper measurement with the 2D frame 310 having the corresponding caliper measurement. For example, the anatomical M-mode generation module 160 may receive the caliper measurement from the caliper measurement module 150 and may generate the anatomical M-mode image based on the direction of the caliper measurement. The anatomical M-mode generation module 160 may then overlay the caliper measurement on the M-mode image at the appropriate position in time based on the selected 2D frame 310 and at the appropriate position in space based on the coordinates of the caliper measurement in the 2D frame 310. The anatomical M-mode generation module 160 presents the M-mode image having the caliper measurement with the selected 2D frame 310 having the corresponding caliper measurement at the display system 134. The generation and presentation of the M-mode image with the caliper measurement occurs substantially in real-time with the placement of the caliper measurement by the caliper measurement module 150 so that the user can verify the positioning of the caliper measurement in both the 2D frame 310 and M-mode image. The caliper measurements and/or generated M-mode image may be stored at archive 138 and/or at any suitable storage medium.

As another example, the anatomical M-mode generation module 160 may receive the caliper measurement from the caliper measurement module 150 and may generate the anatomical M-mode image based on the direction of the caliper measurement. The anatomical M-mode generation module 160 may then automatically process the M-mode image and coordinates from the caliper measurement in the 2D frame 310 to fine tune the position of the caliper measurement in space and time. For example, the anatomical M-mode generation module 160 may include image detection algorithms, one or more deep neural networks and/or may utilize any suitable form of image detection techniques or machine learning processing functionality configured to automatically identify landmarks in the ultrasound image data at different points in time. As an example, the anatomical M-mode generation module 160 may be made up of an input layer, an output layer, and one or more hidden layers in between the input and output layers. Each of the layers may be made up of a plurality of processing nodes that may be referred to as neurons. For example, the input layer may have a neuron for each pixel or a group of pixels from the M-mode image of the organ. The output layer may have a neuron corresponding to each structure and/or anatomical landmark points within the structure of the organ being imaged at various points in time. As an example, if imaging a heart, the output layer may include neurons for end diastole, end systole, unknown, and other, among other things corresponding to different heart structures, such as a pericardium, posterior wall, septal wall, interventricular septum, aortic valve, left ventricle, unknown, and/or other, among other things. Each neuron of each layer may perform a processing function and pass the processed ultrasound image information to one of a plurality of neurons of a downstream layer for further processing. As an example, neurons of a first layer may learn to recognize edges of structure in the ultrasound image data. The neurons of a second layer may learn to recognize shapes based on the detected edges from the first layer. The neurons of a third layer may learn positions of the recognized shapes at various points in time in the M-mode ultrasound image data. The processing performed by the anatomical M-mode generation module 160 deep neural network may identify anatomical landmark points at different points in time with a high degree of probability.

The identified anatomical landmark points at different points in time allow the anatomical M-mode generation module 160 to verify and/or adjust the caliper measurement in the M-mode image. Once the caliper measurement in the M-mode image is verified to be positioned at the appropriate points in space and time, the anatomical M-mode generation module 160 may overlay the caliper measurement on the M-mode image at the appropriate position in space and time and present the M-mode image having the caliper measurement with the selected 2D frame 310 having the corresponding caliper measurement at the display system 134. The generation, verification, and presentation of the M-mode image with the caliper measurement occur substantially in real-time with the placement of the caliper measurement by the caliper measurement module 150 so that the user can verify the positioning of the caliper measurement in both the 2D frame 310 and M-mode image. The caliper measurements and/or generated M-mode image may be stored at archive 138 and/or at any suitable storage medium.

In various embodiments, the anatomical M-mode generation module 160 may adjust the caliper measurement in the M-mode image based, for example, on a user input via the user input module 130 and/or the automatic verification of the caliper measurements based on the image detection algorithms, one or more deep neural networks and/or any suitable form of image detection techniques or machine learning processing functionality. The anatomical M-mode generation module 160 may provide the adjusted caliper measurement to the 2D image selection module 140 for selection of an appropriate frame 310 of the multi-frame 2D image 600 based on the time dimension of the adjusted caliper measurement. The 2D image selection module 140 may provide the appropriate frame 310 to the caliper measurement module 150 and one or both of the 2D image selection module 140 and the anatomical M-mode generation module 160 may provide the adjusted caliper measurement to the caliper measurement module 150. The caliper measurement module 150 may automatically position the adjusted caliper measurement in the appropriate frame 310 of the multi-frame 2D image 600 provided by the 2D image selection module 140 based on the spatial dimension of the adjusted caliper measurement provided by the 2D image selection module 140 and/or the anatomical M-mode generation module 160. Alternatively, the caliper measurement module 150 may independently and automatically position a caliper corresponding to a measurement on the newly-identified 2D frame 310 by processing the newly-selected 2D frame 310 to locate anatomical landmark points for the caliper end points based on the selected measurement by using the image detection algorithms, one or more deep neural networks and/or any suitable form of image detection techniques or machine learning processing functionality configured to automatically identify landmarks in the ultrasound image data as discussed above.

The caliper measurement module 150 may then present the appropriate 2D frame 310 of the multi-frame 2D image 600 having the adjusted caliper measurement with the M-mode image having the adjusted caliper measurement at the display system 134. Additionally and/or alternatively, the caliper measurement module 150 may provide the adjusted caliper measurement automatically and independently determined in the newly-selected 2D frame 310 to the anatomical M-mode generation module 160 for an additional iteration of M-mode image generation and processing by applying the image detection algorithms, one or more deep neural networks and/or any suitable form of image detection techniques or machine learning processing functionality configured to automatically identify landmarks in the M-mode image at different points in time. In a representative embodiment, the caliper measurement module 150 and the anatomical M-mode generation module 160 may perform multiple iterations of the automatic processing to fine tune the automatic placement of the caliper measurement in the appropriate frame 310 of the multi-frame 2D image 600 and the corresponding M-mode image.

The selection of the 2D frame 310 and the presentation of the selected 2D frame 310 with the adjusted caliper measurement occurs substantially in real-time with the placement of the adjusted caliper measurement by the anatomical M-mode generation module 160 so that the user can verify the positioning of the adjusted caliper measurement in both the 2D frame 310 and the M-mode image. The caliper measurement module 150 and/or the anatomical M-mode generation module 160 may store the adjusted caliper measurement in archive 138 and/or at any suitable data storage medium.

In certain embodiments, if a user is not satisfied with the placement of the caliper measurement in the selected frame 310 and/or the M-mode image, the user may manually adjust the caliper measurement via the user input module 130 by selecting new start and end points corresponding with the caliper measurement and/or moving the start point and/or end point of the caliper measurement in either the 2D frame 310 or the M-mode image. The anatomical M-mode generation module 160 may automatically and simultaneously adjust the caliper measurement in the M-mode image in response to any manual adjustment of the caliper measurement in the 2D frame 310. The caliper measurement module 150 may automatically and simultaneously update the caliper measurement in a frame 310 of the multi-frame 2D image 600 in response to any manual adjustment of the caliper measurement in the M-mode image.

Figure 4:
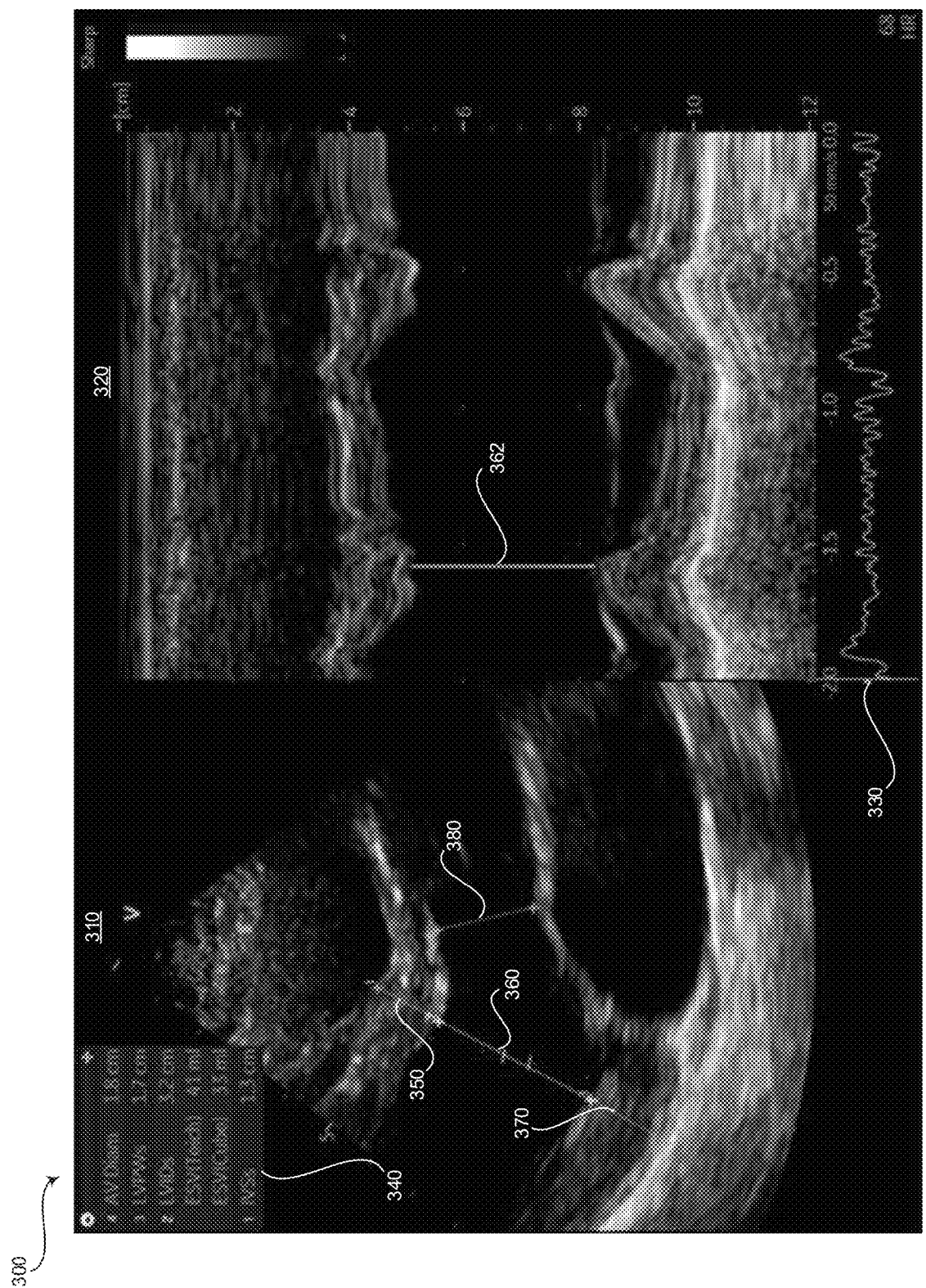
FIG. 4 is an exemplary display of a first selected caliper measurement in a frame of a multi-frame 2D image and the corresponding caliper measurement in an M-mode image, in accordance with various embodiments.
Figure 5:
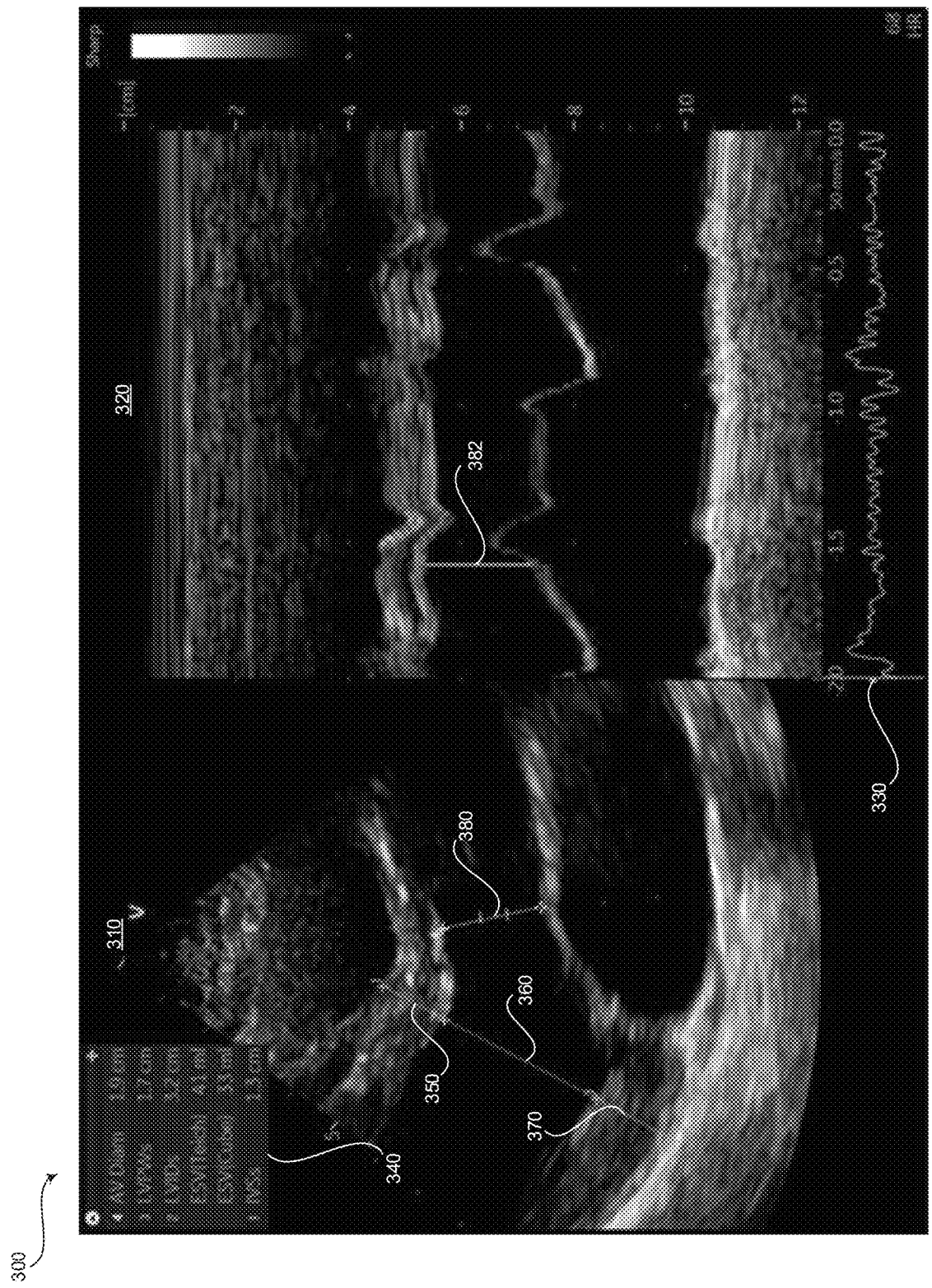
FIG. 5 is an exemplary display of a second selected caliper measurement in a frame of a multi-frame 2D image and the corresponding caliper measurement in an M-mode image, in accordance with various embodiments.

In an exemplary embodiment, the 2D image selection module 140, caliper measurement module 150, and anatomical M-mode generation module 160 of the signal processor 132 comprises suitable logic, circuitry, interfaces and/or code that may be operable to perform and present multiple measurements at the display system 134. In various embodiments, the user may select one of the measurements shown in the 2D frame 310 to navigate to or dynamically generate the corresponding M-mode image having the corresponding caliper measurement. FIG. 4 is an exemplary display 300 of a first selected caliper measurement 360 in a frame 310 of a multi-frame 2D image 600 and the corresponding caliper measurement 362 in an M-mode image 320, in accordance with various embodiments. FIG. 5 is an exemplary display 300 of a second selected caliper measurement 380 in a frame 310 of a multi-frame 2D image 600 and the corresponding caliper measurement 382 in an M-mode image 320, in accordance with various embodiments. Referring to FIGS. 4 and 5, a display 300 that may be presented at one or more display systems 134 or any suitable display includes a frame 310 of a multi-frame 2D image 600, an M-mode image 320, an electrocardiogram (ECG) display 330, a measurement display 340, and caliper measurements 350, 360, 362, 370, 380, 382. The frame 310 of the multi-frame 2D image 600 and the M-mode image 320 may be displayed simultaneously as a split screen or on multiple display systems such that a user may visualize both images simultaneously to assess the measurement information.

The caliper measurements 350, 360, 362, 370, 380, 382 may correspond to the measurement information presented in the measurement display 340. For example, the IVSs measurement of 1.3 centimeters presented in the measurement display 340 corresponds with the interventricular septum at end systole measurement 350 in the frame 310 of the multi-frame 2D image 600. The LVIDs measurement of 3.2 centimeters corresponds with the left ventricle internal diameter at end systole measurement 360 in the frame 310 of the multi-frame 2D image 600 and measurement 362 in the M-mode image 320. The LVPWs measurement of 1.7 centimeters corresponds with the left ventricle posterior wall at end systole measurement 370 in the frame 310 of the multi-frame 2D image 600. The AV Diam measurement of 1.8 centimeters corresponds with the aortic valve diameter measurement 380 in the frame 310 of the multi-frame 2D image 600 and measurement 382 in the M-mode image 320.

Still referring to FIGS. 4 and 5, a user may select a caliper measurement 350, 360, 370, 380 in the frame 310 of the multi-frame 2D image 600 via the user input module 130 and the anatomical M-mode generation module 160 may retrieve and/or generate a corresponding M-mode image 320 having the corresponding caliper measurement 362, 382 overlaid at the appropriate position in time and space in the M-mode image 320. For example, a user may select the left ventricle internal diameter at end systole measurement 360 in the frame 310 of the multi-frame 2D image 600 using a user input module 130 such as a trackball, mousing device, rotary encoder, or the like. As shown in FIG. 4, the anatomical M-mode generation module 160 may retrieve from archive 138 and/or generate a corresponding M-mode image 320 having the corresponding caliper measurement 362 overlaid at the appropriate position in time and space in the M-mode image 320 in response to the selection. The position of the caliper measurement 362 in time is based on the selected frame 310 in the multi-frame 2D image 600 and the position of the caliper measurement 362 in space is based on the coordinates of the caliper measurement 360 in the frame 310. The anatomical M-mode generation module 160 may update the display 300 to provide an M-mode image 320 showing the aortic valve diameter measurement 382 overlaid on the M-mode image 320 as shown in FIG. 5 in response to a user selection of the aortic valve diameter measurement 380 in the frame 310 of the multi-frame 2D image 600. In various embodiments, an indicator may be provided in the ECG display 330 to identify the point in time of the displayed frame 310 of the multi-frame 2D image 600 and the timing of the caliper measurement 362, 382 in the M-mode image 320.

The display 300 provides enhanced visualization of caliper measurements 350, 360, 362, 370, 380, 382 for user verification by simultaneously presenting in substantially real-time a frame 310 of the multi-frame 2D image 600 having the caliper measurement(s) 350, 360, 370, 380, the measurement display 340 having the value(s) corresponding to the caliper measurement(s) 350, 360, 370, 380, the M-mode image 320 with the overlaid caliper measurement(s) 362, 382 corresponding with the selected caliper measurement(s) 350, 360, 370, 380 in the frame 310, and the ECG display 330 identifying the point in time of the displayed frame 310 of the multi-frame 2D image 600 and the timing of the caliper measurement 362, 382 in the M-mode image 320.

Referring again to FIG. 1, the teaching engine 170 may comprise suitable logic, circuitry, interfaces and/or code that may be operable to train the neurons of the deep neural network(s) of the caliper measurement module 150 and/or the anatomical M-mode generation module 160. For example, the teaching engine 170 may train the deep neural networks of the caliper measurement module 150 and/or the anatomical M-mode generation module 160 using databases(s) of classified images. As an example, a caliper measurement module 150 deep neural network may be trained by the teaching engine 170 with images of a particular organ to train the caliper measurement module 150 with respect to the characteristics of the particular organ, such as the appearance of structure edges, the appearance of structure shapes based on the edges, the positions of the shapes in the ultrasound image data, and the like. In certain embodiments, the organ may be a heart and the structural information may include information regarding the edges, shapes, positions, and timing information (e.g., end diastole, end systole, etc.) of a pericardium, posterior wall, septal wall, interventricular septum, aortic valve, left ventricle, and/or the like. In various embodiments, the databases of training images may be stored in the archive 138 or any suitable data storage medium. In certain embodiments, the training engine 170 and/or training image databases may be external system(s) communicatively coupled via a wired or wireless connection to the ultrasound system 100.

Figure 2:
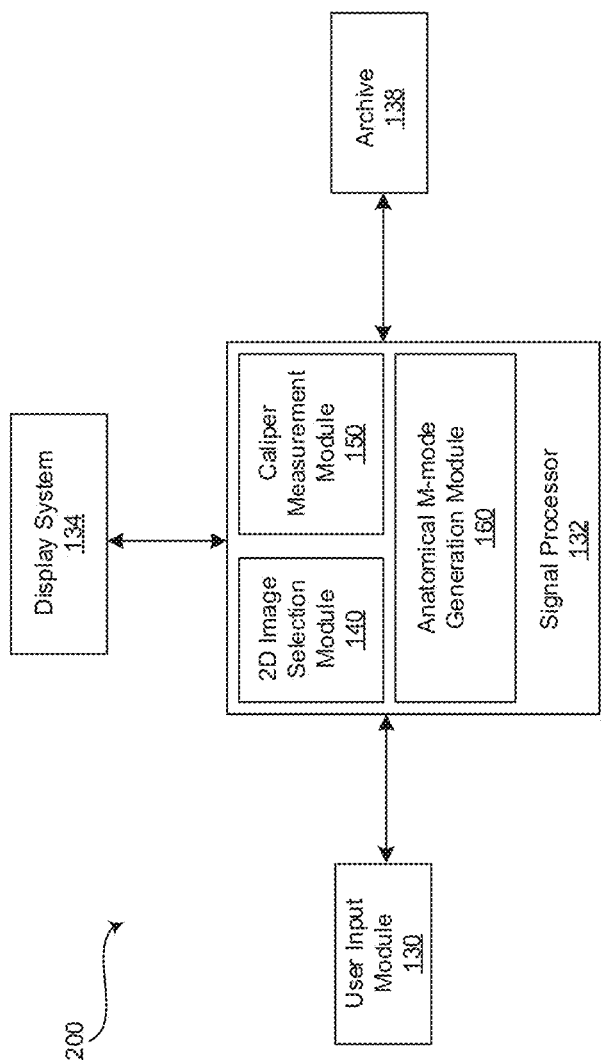
FIG. 2 is a block diagram of an exemplary medical workstation that is operable to synchronize caliper measurements in a multi-frame 2D image and an M-mode image, in accordance with various embodiments.

FIG. 2 is a block diagram of an exemplary medical workstation 200 that is operable to synchronize caliper measurements 350, 360, 362, 370, 380, 382 in a multi-frame 2D image 600 and an M-mode image 320, in accordance with various embodiments. In various embodiments, components of the medical workstation 200 may share various characteristics with components of the ultrasound system 100, as illustrated in FIG. 1 and described above. Referring to FIG. 2, the medical workstation 200 comprises a display system 134, a signal processor 132, an archive 138, and a user input module 130, among other things. Components of the medical workstation 200 may be implemented in software, hardware, firmware, and/or the like. The various components of the medical workstation 200 may be communicatively linked. Components of the medical workstation 200 may be implemented separately and/or integrated in various forms. For example, the display system 134 and the user input module 130 may be integrated as a touchscreen display.

The display system 134 may be any device capable of communicating visual information to a user. For example, a display system 134 may include a liquid crystal display, a light emitting diode display, and/or any suitable display or displays. The display system 134 can be operable to display information from the signal processor 132 and/or archive 138, such as medical images, caliper measurements 340, 350, 360, 362, 370, 380, 382, or any suitable information.

The signal processor 132 may be one or more central processing units, microprocessors, microcontrollers, and/or the like. The signal processor 132 may be an integrated component, or may be distributed across various locations, for example. The signal processor 132 comprises a 2D image selection module 140, a caliper measurement module 150, and an anatomical M-mode generation module 160, as described above with reference to FIG. 1, and may be capable of receiving input information from a user input module 130 and/or archive 138, generating an output displayable by a display system 134, and manipulating the output in response to input information from a user input module 130, among other things. The signal processor 132, 2D image selection module 140, caliper measurement module 150, and/or anatomical M-mode generation module 160 may be capable of executing any of the method(s) and/or set(s) of instructions discussed herein in accordance with the various embodiments, for example.

The archive 138 may be one or more computer-readable memories integrated with the medical workstation 200 and/or communicatively coupled (e.g., over a network) to the medical workstation 200, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores medical image data and instructions for synchronizing caliper measurements 350, 360, 362, 370, 380, 382 in multi-frame 2D images 600 and M-mode images 320, for example.

The user input module 130 may include any device(s) capable of communicating information from a user and/or at the direction of the user to the signal processor 132 of the medical workstation 200, for example. As discussed above with respect to FIG. 1, the user input module 130 may include a touch panel, button(s), a mousing device, keyboard, rotary encoder, trackball, camera, voice recognition, and/or any other device capable of receiving a user directive.

Figure 6:
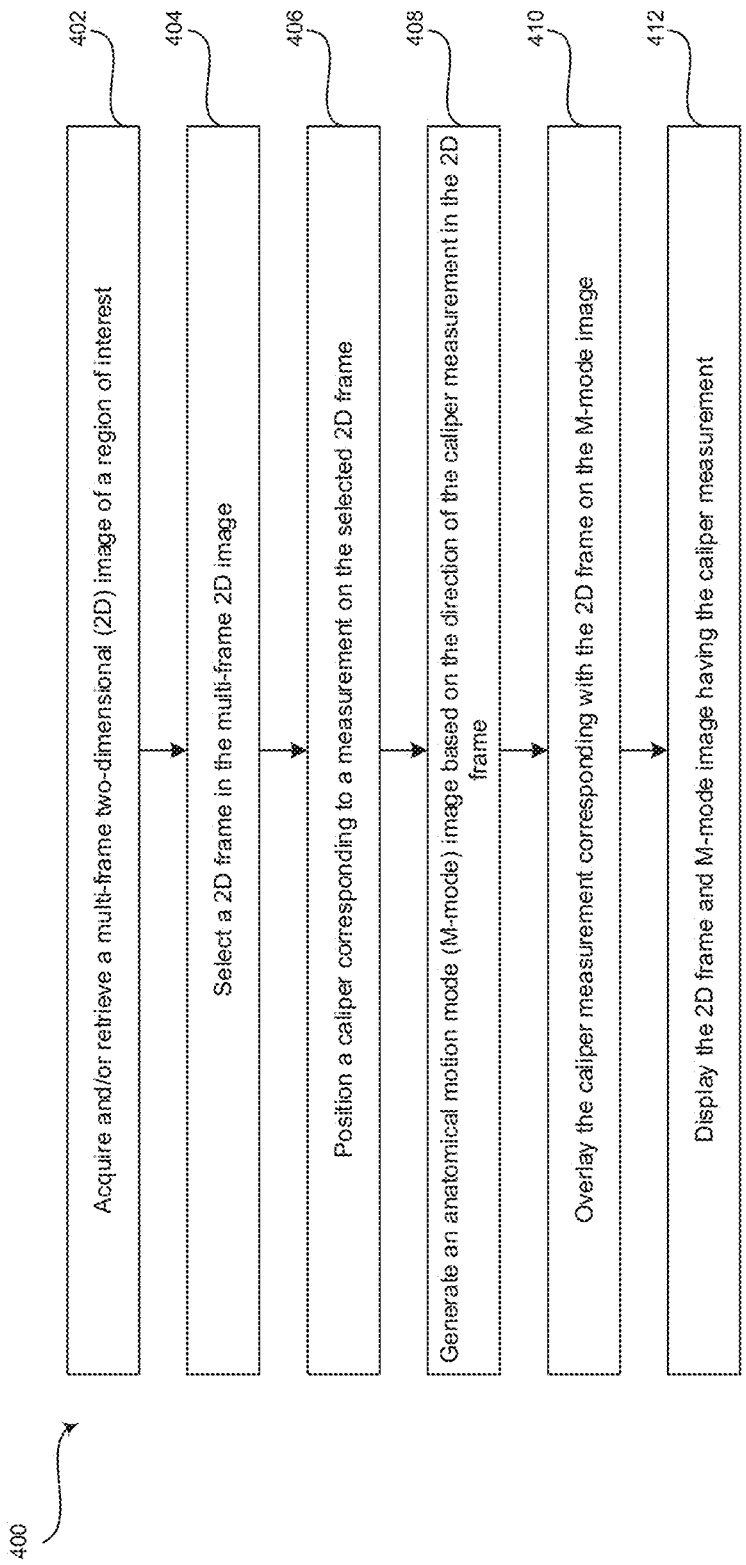
FIG. 6 is a flow chart illustrating exemplary steps that may be utilized for synchronizing caliper measurements in a multi-frame 2D image and an M-mode image, in accordance with exemplary embodiments.

FIG. 6 is a flow chart 400 illustrating exemplary steps 402-412 that may be utilized for synchronizing caliper measurements 350, 360, 362, 370, 380, 382 in a multi-frame 2D image 600 and an M-mode image 320, in accordance with exemplary embodiments. Referring to FIG. 6, there is shown a flow chart 400 comprising exemplary steps 402 through 412. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 402, an ultrasound system 100 may acquire and/or a signal processor 132 may retrieve a multi-frame 2D image 600 of a region of interest. For example, the ultrasound system 100 may acquire a multi-frame 2D image 600 with an ultrasound probe 104. The ultrasound probe 104 may provide the multi-frame 2D image 600 corresponding with at least a substantial portion of an organ, such as a heart or any suitable organ. As another example, a signal processor 132 of a workstation 200 or ultrasound system 100 may retrieve a multi-frame 2D image 600 from an archive 138 or any suitable data storage medium.

At step 404, the signal processor 132 of the ultrasound system 100 or workstation 200 may select a frame 310 of the multi-frame 2D image 600. For example, a 2D image selection module 140 of the signal processor 132 may receive a directive from a user input module 130, such as a rotary encoder, button, mousing device, trackball, or the like, for selecting one of the frames 310 of the multi-frame 2D image 600. In an exemplary embodiment of an imaged heart, the selected frame 310 may correspond with end diastole or end systole, among other things. The user input module 130 may provide the frame selection after the user navigates through the multi-frame 2D image 600 to identify the frame 310 corresponding with the desired time. Additionally and/or alternatively, the frame 310 may be automatically identified by the 2D image selection module 140 of the signal processor 132 based on a selected measurement type. As an example, the 2D image selection module 140 of the signal processor 132 may perform a course estimation of end diastolic/end systolic frame time by using detected heart cycle start and end points and apply a heuristic formula for estimating the time of a cardiac phase.

At step 406, the signal processor 132 of the ultrasound system may position a caliper corresponding to a measurement on the selected 2D frame 310. For example, a caliper measurement module 140 of the signal processor 132 may position the caliper by setting caliper start and end points and a line connecting the end points in the frame 310 of the multi-frame 2D image 600 selected at step 404. The caliper may be positioned by the caliper measurement module 150 in response to a user input via a user input module 130 selecting the start and end points or automatically by processing the frame 310 to locate anatomical landmark points for the caliper start and end points based on the measurement type.

At step 408, the signal processor 132 may generate an anatomical M-mode image 320 based on the direction of the caliper measurement 350, 360, 370, 380 in the 2D frame 310. For example, an anatomical M-mode generation module 160 of the signal processor 132 may use the caliper measurement direction to reconstruct an M-mode image 320 from the multi-frame 2D image data 600. The direction of the caliper measurement 350, 360, 370, 380 identifies the spatial dimension in the multi-frame 2D image data 600 and the plurality of frames 310 of the multi-frame 2D image data 600 provide the time dimension for the M-mode image 320.

At step 410, the signal processor 132 may overlay the caliper measurement 362, 382 corresponding with the caliper measurement 350, 360, 370, 380 in the 2D frame 310 on the M-mode image 320. For example, the anatomical M-mode generation module 160 of the signal processor 132 may overlay the caliper measurement 362, 382 corresponding with the caliper measurement 350, 360, 370, 380 from the frame 310 of the multi-frame 2D image 600 on the M-mode image 320 generated at step 408. The overlaid caliper measurement 362, 382 may be positioned in the time dimension of the M-mode image 320 based on the selected frame 310 of the multi-frame 2D image 600 and in the spatial dimension of the M-mode image 320 based on the coordinates of the caliper measurement 350, 360, 370, 380 in the frame 310 of the multi-frame 2D image 600.

At step 412, the signal processor 132 may present the 2D frame 310 and M-mode image 320 each having the caliper measurement 350, 360, 362, 370, 380, 382. For example, an anatomical M-mode generation module 160 of the signal processor 132 may be configured to present the selected frame 310 of the multi-frame 2D image 600 having the caliper measurement 350, 360, 370, 380 and the M-mode image 320 having the corresponding caliper measurement 362, 382 at a display system 134 of the ultrasound system 100 or workstation 200. In various embodiments, the 2D frame 310 may include multiple caliper measurements 360, 360, 370, 380 and the anatomical M-mode generation module 160 may selectively retrieve and/or generate an M-mode image 320 having a corresponding caliper measurement 362, 382 in response to a user selection of one of the caliper measurements 360, 360, 370, 380 in the 2D frame 310. In a representative embodiment, the display 300 of the 2D frame 310 and M-mode image 320 each having the caliper measurement 350, 360, 362, 370, 380, 382 may also include additional information such as an ECG display 330, a measurement display 340, and the like. For example, the ECG display 330 may include an indicator to identify the point in time of the displayed frame 310 of the multi-frame 2D image 600 and the position of the caliper measurement 362, 382 in the M-mode image 320. The measurement display 340 may include value(s) corresponding to the caliper measurement(s) 350, 360, 362, 370, 380, 382. The frame 310 of the multi-frame 2D image 600 and the M-mode image 320 along with the caliper measurements 350, 360, 362, 370, 380, 382 may be displayed simultaneously as a split screen or on multiple display systems 134 such that a user may visualize both images simultaneously to assess the measurement information. The display 300 provides enhanced visualization of caliper measurements 350, 360, 362, 370, 380, 382 for user verification by simultaneously presenting in substantially real-time a frame 310 of the multi-frame 2D image 600 having the caliper measurement(s) 350, 360, 370, 380 and the M-mode image 320 with the overlaid caliper measurement(s) 362, 382 corresponding with the selected caliper measurement(s) 350, 360, 370, 380 in the frame 310.

Figure 7:
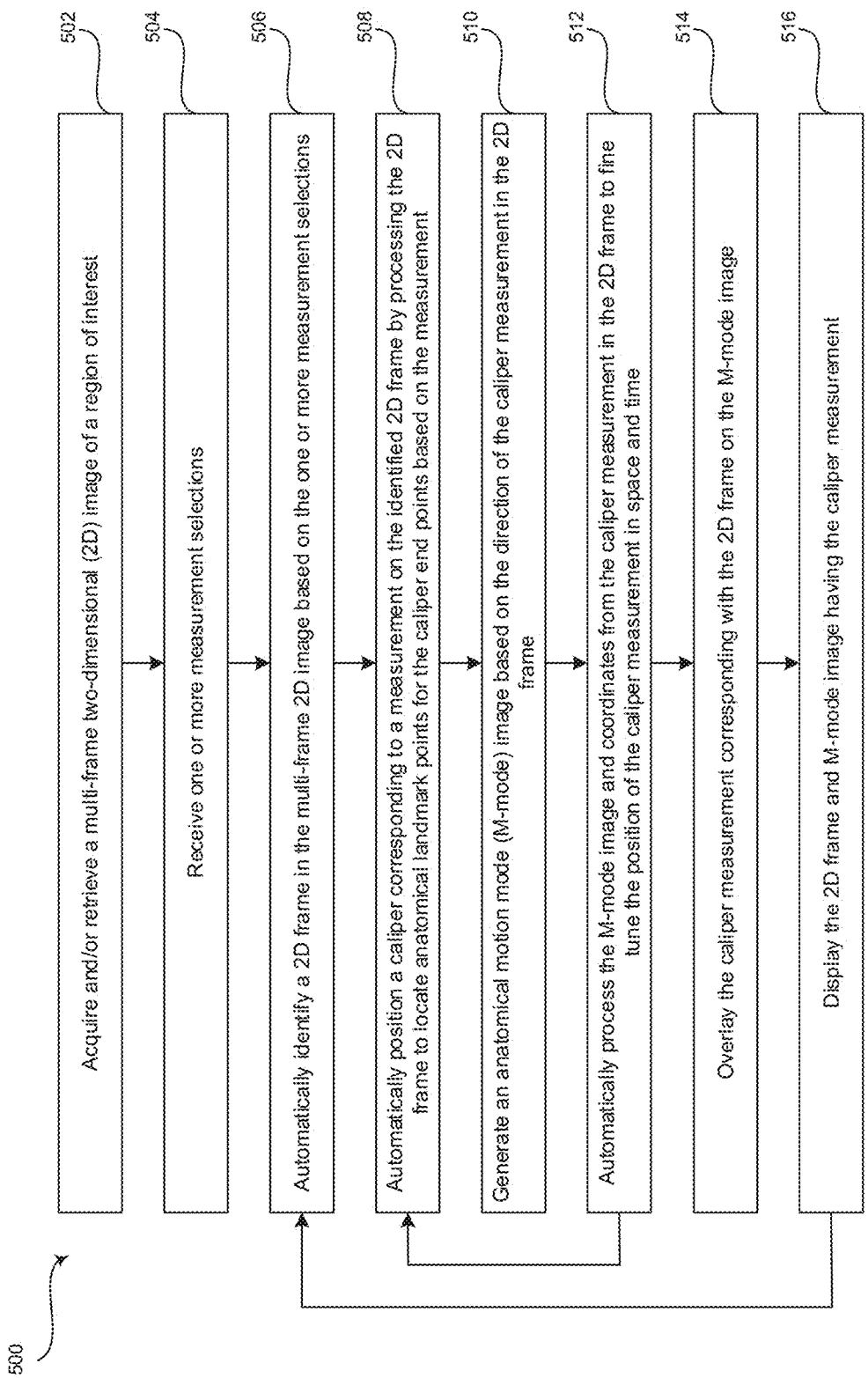
FIG. 7 is a flow chart illustrating exemplary steps that may be utilized for synchronizing caliper measurements in a multi-frame 2D image and an M-mode image, in accordance with exemplary embodiments.

FIG. 7 is a flow chart 500 illustrating exemplary steps 502-516 that may be utilized for synchronizing caliper measurements 350, 360, 362, 370, 380, 382 in a multi-frame 2D image 600 and an M-mode image 320, in accordance with exemplary embodiments. Referring to FIG. 7, there is shown a flow chart 500 comprising exemplary steps 502 through 516. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 502, an ultrasound system 100 may acquire and/or a signal processor 132 may retrieve a multi-frame 2D image 600 of a region of interest. For example, the ultrasound system 100 may acquire a multi-frame 2D image 600 with an ultrasound probe 104. The ultrasound probe 104 may provide the multi-frame 2D image 600 corresponding with at least a substantial portion of an organ, such as a heart or any suitable organ. As another example, a signal processor 132 of a workstation 200 or ultrasound system 100 may retrieve a multi-frame 2D image 600 from an archive 138 or any suitable data storage medium.

At step 504, the signal processor 132 of the ultrasound system or workstation 200 may receive one or more caliper measurement selections. For example, a 2D image selection module 140 of the signal processor 132 may receive, via a user input module 130, caliper measurement selection(s) such as an interventricular septum at end systole (IVSs) measurement 350, a left ventricle internal diameter at end systole (LVIDs) measurement 360, a left ventricle posterior wall at end systole (LVPWs) measurement 370, an aortic valve diameter (AV Diam) measurement 380, or any suitable measurement of the heart or any suitable organ or structure.

At step 506, the signal processor 132 may automatically identify a 2D frame 310 in the multi-frame 2D image 600 based on the one or more caliper measurement selections. For example, the 2D image selection module 140 of the signal processor 132 may automatically identify a frame 310 of the multi-frame 2D image 600 based on a selected measurement type. As an example, for a measurement performed of the heart at end systole, the 2D image selection module 140 of the signal processor 132 may perform a course estimation of end systolic frame time by using detected heart cycle start and end points and apply a heuristic formula for estimating the time of a cardiac phase.

At step 508, the signal processor 132 may automatically position a caliper corresponding to a measurement 350, 360, 370, 380 on the identified 2D frame 310 by processing the 2D frame 310 to locate anatomical landmark points for the caliper end points based on the measurement. For example, a caliper measurement module 150 of the signal processor may include image detection algorithms, one or more deep neural networks and/or may utilize any suitable form of image detection techniques or machine learning processing functionality configured to automatically identify landmarks in the frame 310 of the multi-frame 2D image 600 selected at step 506. In an exemplary embodiment, the caliper measurement module 150 may be made up of an input layer, an output layer, and one or more hidden layers in between the input and output layers. Each of the layers may be made up of a plurality of processing nodes that may be referred to as neurons. Each neuron of each layer may perform a processing function and pass the processed ultrasound image information to one of a plurality of neurons of a downstream layer for further processing. The output layer may have a neuron corresponding to each structure and/or anatomical landmark points within the structure of the organ being imaged. The caliper measurement module 150 may overlay a line connecting the anatomical landmark points corresponding with a selected measurement on the 2D frame 310 and a measurement 350, 360, 370, 380 corresponding with the distance between the points may be presented by the caliper measurement module 150 at the display system 134 with the 2D frame 310.

At step 510, the signal processor 132 may generate an anatomical M-mode image 320 based on the direction of the caliper measurement 350, 360, 370, 380 in the 2D frame 310. For example, an anatomical M-mode generation module 160 of the signal processor 132 may use the caliper measurement direction from step 508 to reconstruct an M-mode image 320 from the multi-frame 2D image data 600. The direction of the caliper measurement 350, 360, 370, 380 identifies the spatial dimension in the multi-frame 2D image data 600 and the plurality of frames 310 of the multi-frame 2D image data 600 provide the time dimension for the M-mode image 320.

At step 512, the signal processor 132 may automatically process the M-mode image 320 and coordinates from the caliper measurement 350, 360, 370, 380 in the 2D frame 310 to fine tune the position of the caliper measurement 350, 360, 362, 370, 380, 382 in space and time. For example, the anatomical M-mode generation module 160 of the signal processor 132 may include image detection algorithms, one or more deep neural networks and/or may utilize any suitable form of image detection techniques or machine learning processing functionality configured to automatically identify landmarks in the ultrasound image data at different points in time. The anatomical M-mode generation module 160 may be made up of an input layer, an output layer, and one or more hidden layers in between the input and output layers. Each of the layers may be made up of a plurality of processing nodes that may be referred to as neurons. Each neuron of each layer may perform a processing function and pass the processed ultrasound image information to one of a plurality of neurons of a downstream layer for further processing. The output layer may have a neuron corresponding to each structure and/or anatomical landmark points within the structure of the organ being imaged at various points in time. The identified anatomical landmark points at different points in time allow the anatomical M-mode generation module 160 to verify and/or adjust the caliper measurement in the M-mode image. If the anatomical M-mode generation module 160 adjusts the caliper measurement, the anatomical M-mode generation module 160 may provide the adjusted caliper measurement to the 2D image selection module 140 for selection of an appropriate frame 310 of the multi-frame 2D image 600 based on the time dimension of the adjusted caliper measurement. The process may then return to step 508 where the appropriate frame 310 of the multi-frame 2D image 600 is provided to the caliper measurement module 150 for automatic positioning of the caliper in the appropriate frame 310 identified by the 2D image selection module 140 based on the automatic processing performed by the anatomical M-mode generation module 160. Steps 508 through 512 may be repeated until the automatic positioning of the caliper performed by the caliper measurement module 150 at step 508 is verified by the automatic processing of the M-mode image 320 by the anatomical M-mode generation module 160 at step 512.

At step 514, the signal processor 132 may overlay the caliper measurement 362, 382 corresponding with the caliper measurement 350, 360, 370, 380 in the 2D frame 310 on the M-mode image 320. For example, the anatomical M-mode generation module 160 of the signal processor 132 may overlay the caliper measurement 362, 382 corresponding with the caliper measurement 350, 360, 370, 380 from the frame 310 of the multi-frame 2D image 600 and verified by the anatomical M-mode generation module 160 at step 512 on the M-mode image 320 generated at step 510. The overlaid caliper measurement 362, 382 may be positioned based on the automatic positioning of the caliper at step 508 and the automatic processing of the M-mode image 320 performed at step 512.

At step 516, the signal processor 132 may present the 2D frame 310 and M-mode image 320 each having the caliper measurement 350, 360, 362, 370, 380, 382. For example, an anatomical M-mode generation module 160 of the signal processor 132 may be configured to present the selected frame 310 of the multi-frame 2D image 600 having the caliper measurement 350, 360, 370, 380 and the M-mode image 320 having the corresponding caliper measurement 362, 382 at a display system 134 of the ultrasound system 100 or workstation 200. If multiple caliper measurements were selected at step 504, the process may return to step 506 to repeat steps 506 through 516 for each of the selected measurements. In various embodiments having multiple caliper measurements 360, 360, 370, 380 in the 2D frame 310, the anatomical M-mode generation module 160 may selectively retrieve and/or generate an M-mode image 320 having a corresponding caliper measurement 362, 382 in response to a user selection of one of the caliper measurements 360, 360, 370, 380 in the 2D frame 310. In a representative embodiment, the display 300 of the 2D frame 310 and M-mode image 320 each having the caliper measurement 350, 360, 362, 370, 380, 382 may also include additional information such as an ECG display 330, a measurement display 340, and the like. For example, the ECG display 330 may include an indicator to identify the point in time of the displayed frame 310 of the multi-frame 2D image 600 and the position of the caliper measurement 362, 382 in the M-mode image 320. The measurement display 340 may include value(s) corresponding to the caliper measurement(s) 350, 360, 362, 370, 380, 382. The frame 310 of the multi-frame 2D image 600 and the M-mode image 320 along with the caliper measurements 350, 360, 362, 370, 380, 382 may be displayed simultaneously as a split screen or on multiple display systems 134 such that a user may visualize both images simultaneously to assess the measurement information. The display 300 provides enhanced visualization of caliper measurements 350, 360, 362, 370, 380, 382 for user verification by simultaneously presenting in substantially real-time a frame 310 of the multi-frame 2D image 600 having the caliper measurement(s) 350, 360, 370, 380 and the M-mode image 320 with the overlaid caliper measurement(s) 362, 382 corresponding with the selected caliper measurement(s) 350, 360, 370, 380 in the frame 310.

Aspects of the present disclosure provide a method 400, 500 and system 100, 200 for synchronizing caliper measurements 350, 360, 362, 370, 380, 382 in a multi-frame 2D image 600 and an M-mode image 320. In accordance with various embodiments, the method 400, 500 may comprise selecting 404, 506, by at least one processor 132, 140, a frame 310 of a multi-frame two-dimensional image 600 of a region of interest. The method 400, 500 may comprise positioning 406, 508, by the at least one processor 132, 150, a first caliper measurement 350, 360, 370, 380 on the selected frame 310. The method 400, 500 may comprise generating 408, 510, by the at least one processor 132, 160, an anatomical motion mode image 320 based on a direction of the first caliper measurement 350, 360, 370, 380. The method 400, 500 may comprise automatically overlaying 410, 514, by the at least one processor 132, 160, a second caliper measurement 362, 382 on the anatomical motion mode image 320, the second caliper measurement 362, 382 corresponding with the first caliper measurement 350, 360, 370, 380 on the selected frame 310. The method 400, 500 may comprise presenting 412, 516 the selected frame 310 having the first caliper measurement 350, 360, 370, 380 simultaneously with the anatomical motion mode image 320 having the second caliper measurement 362, 382 at a display system 134.

In various embodiments, the method 400, 500 may comprise positioning 406, 508, by the at least one processor 132, 150, a third caliper measurement 350, 360, 370, 380 on the selected frame 310. The method 400, 500 may comprise generating 408, 510, by the at least one processor 132, 160, an additional anatomical motion mode image 320 based on a direction of the third caliper measurement 350, 360, 370, 380. The method 400, 500 may comprise automatically overlaying 410, 514, by the at least one processor 132, 160, a fourth caliper measurement 362, 382 on the additional anatomical motion mode image 320. The fourth caliper measurement 362, 382 may correspond with the third caliper measurement 350, 360, 370, 380 on the selected frame 310. The method 400, 500 may comprise presenting 412, 516 the selected frame 310 having the first caliper measurement 350, 360, 370, 380 and the third caliper measurement 350, 360, 370, 380 simultaneously with the additional anatomical motion mode image 320 having the fourth caliper measurement 362, 382 at the display system 134.

In certain embodiment, the method 400, 500 may comprise receiving, by the at least one processor 132, a selection of one of the first caliper measurement 350, 360, 370, 380 or the third caliper measurement 350, 360, 370, 380. The method 400, 500 may comprise presenting 412, 516 the selected frame 310 having the first caliper measurement 350, 360, 370, 380 and the third caliper measurement 350, 360, 370, 380 simultaneously with the anatomical motion mode image 320 having the second caliper measurement 362, 382 at the display system 134 if the selection is the first caliper measurement 350, 360, 370, 380. The method 400, 500 may comprise presenting 362, 382 the selected frame 310 having the first caliper measurement 350, 360, 370, 380 and the third caliper measurement 350, 360, 370, 380 simultaneously with the additional anatomical motion mode image 320 having the fourth caliper measurement 362, 382 at the display system 134 if the selection is the third caliper measurement 350, 360, 370, 380.

In a representative embodiment, the method 400, 500 may comprise receiving 402, 502, by the at least one processor 132, 140, the multi-frame two-dimensional image 600 of the region of interest from one of an ultrasound probe 104 or an archive 138. In an exemplary embodiment, the method 400, 500 may comprise receiving 406, 504, by the at least one processor 132, 140, 150, at least one measurement selection. In various embodiments, the at least one processor 132, 140 automatically selects the frame 310 based on the at least one measurement selection. In certain embodiments, the at least one processor 132, 150 automatically positions the first caliper measurement 350, 360, 370, 380 on the selected frame 310 by processing the selected frame 310 to locate anatomical landmark points corresponding to measurement end points defined by the at least one measurement selection. In a representative embodiments, the anatomical landmark points are automatically located by the at least one processor 132, 150 based on machine-learning algorithms.

In an exemplary embodiment, the method 500 comprises automatically processing 512, by the at least one processor 132, 160, the anatomical motion mode image 320 and coordinates of the first caliper measurement 350, 360, 370, 380 based on machine-learning algorithms to determine whether the selected frame 310 is a correct frame. The method 400, 500 comprises adjusting 506-512, by the at least one processor 132, 140, 150, 160, the first caliper measurement 350, 360, 370, 380 if the selected frame is not the correct frame by selecting, by the at least one processor 132, 140, 160, a new frame 310 of the multi-frame two-dimensional image 600 of the region of interest based on temporal information of the anatomical motion mode image 320, and positioning 508, by the at least one processor 132, 150, the first caliper measurement 350, 360, 370, 380 on the selected new frame 310. In various embodiments, the anatomical motion mode image 320 having the second caliper measurement 362, 382 is presented at the display system 134 at substantially a same time as the first caliper measurement 350, 360, 370, 380 is positioned on the selected frame 310.

Various embodiments provide a system 100, 200 for synchronizing caliper measurements 350, 360, 362, 370, 380, 382 in a multi-frame 2D image 600 and an M-mode image 320. The system 100, 200 may comprise at least one processor 132, 140, 150, 160 and a display system 134. The at least one processor 132, 140 may be configured to select a frame 310 of a multi-frame two-dimensional image 600 of a region of interest. The at least one processor 132, 150 may be configured to position a first caliper measurement 350, 360, 370, 380 on the selected frame 310. The at least one processor 132, 160 may be configured to generate an anatomical motion mode image 320 based on a direction of the caliper measurement 350, 360, 370, 380. The at least one processor 132, 160 may be configured to automatically overlay a second caliper measurement 362, 182 on the anatomical motion mode image 320, the second caliper measurement 362, 182 corresponding with the first caliper measurement 350, 360, 370, 380 on the selected frame 310. The display system may be configured to present the selected frame 310 having the first caliper measurement 350, 360, 370, 380 simultaneously with the anatomical motion mode image 320 having the second caliper measurement 362, 382.

In certain embodiments, the at least one processor 132, 140, 150 may be configured to receive at least one measurement selection, and automatically select the frame 310 based on the at least one measurement selection. In a representative embodiment, the at least one processor 132, 140, 150 is configured to receive at least one measurement selection, and automatically position the first caliper measurement 350, 360, 370, 380 on the selected frame 310 by processing the selected frame 310 to locate anatomical landmark points corresponding to measurement end points defined by the at least one measurement selection. In an exemplary embodiment, the at least one processor 132, 150 is configured to automatically locate the anatomical landmark points based on machine-learning algorithms.

In various embodiment, the at least one processor 132, 160 may be configured to automatically process the anatomical motion mode image 320 and coordinates of the first caliper measurement 350, 360, 370, 380 based on machine-learning algorithms to determine whether the selected frame 310 is a correct frame. The at least one processor 132, 140, 150, 160 may be configured to adjust the first caliper measurement 350, 360, 370, 380 if the selected frame 310 is not the correct frame by selecting a new frame 310 of the multi-frame two-dimensional image 600 of the region of interest based on temporal information of the anatomical motion mode image 320, and positioning the first caliper measurement 350, 360, 370, 380 on the selected new frame 310. In certain embodiments, the display system 134 presents the anatomical motion mode image 320 having the second caliper measurement 362, 382 at substantially a same time as the first caliper measurement 350, 360, 370, 380 is positioned on the selected frame 310. In a representative embodiment, the system 100, 200 may comprise one or both of an ultrasound probe 104 and an archive 138 configured to provide the at least one processor 132, 140 with the multi-frame two-dimensional image 600 of the region of interest.

Certain embodiments provide a non-transitory computer readable medium having stored thereon, a computer program having at least one code section. The at least one code section is executable by a machine for causing the machine to perform steps 400, 500. The steps 400, 500 may comprise selecting 404, 506 a frame 310 of a multi-frame two-dimensional image 600 of a region of interest. The steps 400, 500 may comprise positioning 406, 508 a first caliper measurement 350, 360, 370, 380 on the selected frame 310. The steps 400, 500 may comprise generating 408, 510 an anatomical motion mode image 320 based on a direction of the first caliper measurement 350, 360, 370, 380. The steps 400, 500 may comprise automatically overlaying 410, 514 a second caliper measurement 362, 382 on the anatomical motion mode image 320, the second caliper measurement 362, 382 corresponding with the first caliper measurement 350, 360, 370, 380 on the selected frame 310. The steps 400, 500 may comprise presenting 412, 516 the selected frame 310 having the first caliper measurement 350, 360, 370, 380 simultaneously with the anatomical motion mode image 320 having the second caliper measurement 362, 382 at a display system 134.

In an exemplary embodiment, the steps 400, 500 may comprise receiving 504 at least one measurement selection. The frame 310 may be automatically selected 506 based on the at least one measurement selection. In various embodiments, the steps 400, 500 may comprise receiving 504 at least one measurement selection. The first caliper measurement 350, 360, 370, 380 may be automatically positioned 508 on the selected frame 310 by processing the selected frame 310 to locate anatomical landmark points corresponding to measurement end points defined by the at least one measurement selection. The anatomical landmark points may be automatically located based on machine-learning algorithms. In certain embodiments, the steps 400, 500 may comprise automatically processing 512 the anatomical motion mode image 320 and coordinates of the first caliper measurement 350, 360, 370, 380 based on machine-learning algorithms to determine whether the selected frame 310 is a correct frame. The steps 400, 500 may comprise adjusting 508-512 the first caliper measurement 350, 360, 370, 380 if the selected frame 310 is not the correct frame by selecting 512 a new frame 310 of the multi-frame two-dimensional image 600 of the region of interest based on temporal information of the anatomical motion mode image 320, and positioning 508 the first caliper measurement 350, 360, 370, 380 on the selected new frame 310. In a representative embodiment, the anatomical motion mode image 320 having the second caliper measurement 362, 382 is presented at the display system 134 at substantially a same time as the first caliper measurement 350, 360, 370, 380 is positioned on the selected frame 310.

As referred to herein, the terms "substantially a same time," "substantially in real-time," and the like refer to the small amount of time offset inherent to processing delays dependent on the processing power of the at least one processor 132, 140, 150, 160. As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set $\{(x), (y), (x, y)\}$. As another example, "x, y, and/or z" means any element of the seven-element set $\{(x), (y), (z), (x, y), (x, z), (y, z), (x, y, z)\}$. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein synchronizing caliper measurements in a multi-frame 2D image and an M-mode image.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method comprising:
    selecting, by at least one processor, a frame of a multi-frame two-dimensional image of a region of interest;
    positioning, by the at least one processor, a first caliper measurement on the selected frame;
    generating, by the at least one processor, an anatomical motion mode image based on a direction of the first caliper measurement;
    automatically overlaying, by the at least one processor, a second caliper measurement on the anatomical motion mode image, the second caliper measurement corresponding with the first caliper measurement on the selected frame; and
    presenting the selected frame having the first caliper measurement simultaneously with the anatomical motion mode image having the second caliper measurement at a display system.

2. The method of claim 1, comprising:
    positioning, by the at least one processor, a third caliper measurement on the selected frame;
    generating, by the at least one processor, an additional anatomical motion mode image based on a direction of the third caliper measurement;
    automatically overlaying, by the at least one processor, a fourth caliper measurement on the additional anatomical motion mode image, the fourth caliper measurement corresponding with the third caliper measurement on the selected frame; and
    presenting the selected frame having the first caliper measurement and the third caliper measurement simultaneously with the additional anatomical motion mode image having the fourth caliper measurement at the display system.

3. The method of claim 2, comprising:
    receiving, by the at least one processor, a selection of one of the first caliper measurement or the third caliper measurement,
    presenting the selected frame having the first caliper measurement and the third caliper measurement simultaneously with the anatomical motion mode image having the second caliper measurement at the display system if the selection is the first caliper measurement, and
    presenting the selected frame having the first caliper measurement and the third caliper measurement simultaneously with the additional anatomical motion mode image having the fourth caliper measurement at the display system if the selection is the third caliper measurement.

4. The method of claim 1, comprising receiving, by the at least one processor, at least one measurement selection, wherein the at least one processor automatically selects the frame based on the at least one measurement selection.

5. The method of claim 1, comprising receiving, by the at least one processor, at least one measurement selection, wherein the at least one processor automatically positions the first caliper measurement on the selected frame by processing the selected frame to locate anatomical landmark points corresponding to measurement end points defined by the at least one measurement selection.

6. The method of claim 5, wherein the anatomical landmark points are automatically located by the at least one processor based on machine-learning algorithms.

7. The method of claim 1, comprising:
automatically processing, by the at least one processor, the anatomical motion mode image and coordinates of the first caliper measurement based on machine-learning algorithms to determine whether the selected frame is a correct frame; and
adjusting, by the at least one processor, the first caliper measurement if the selected frame is not the correct frame by:
selecting, by the at least one processor, a new frame of the multi-frame two-dimensional image of the region of interest based on temporal information of the anatomical motion mode image, and
positioning, by the at least one processor, the first caliper measurement on the selected new frame.

8. The method of claim 1, wherein the anatomical motion mode image having the second caliper measurement is presented at the display system at substantially a same time as the first caliper measurement is positioned on the selected frame.

9. A system comprising:
at least one processor configured to:
select a frame of a multi-frame two-dimensional image of a region of interest, position a first caliper measurement on the selected frame,
generate an anatomical motion mode image based on a direction of the caliper measurement, and
automatically overlay a second caliper measurement on the anatomical motion mode image, the second caliper measurement corresponding with the first caliper measurement on the selected frame; and
a display system configured to present the selected frame having the first caliper measurement simultaneously with the anatomical motion mode image having the second caliper measurement.

10. The system of claim 9, wherein the at least one processor is configured to:
receive at least one measurement selection, and
automatically select the frame based on the at least one measurement selection.

11. The system of claim 9, wherein the at least one processor is configured to:
receive at least one measurement selection, and
automatically position the first caliper measurement on the selected frame by processing the selected frame to locate anatomical landmark points corresponding to measurement end points defined by the at least one measurement selection.

12. The system of claim 11, wherein the at least one processor is configured to automatically locate the anatomical landmark points based on machine-learning algorithms.

13. The system of claim 9, wherein the at least one processor is configured to:
automatically process the anatomical motion mode image and coordinates of the first caliper measurement based on machine-learning algorithms to determine whether the selected frame is a correct frame; and
adjust the first caliper measurement if the selected frame is not the correct frame by:
selecting a new frame of the multi-frame two-dimensional image of the region of interest based on temporal information of the anatomical motion mode image, and
positioning the first caliper measurement on the selected new frame.

14. The system of claim 9, wherein the display system presents the anatomical motion mode image having the second caliper measurement at substantially a same time as the first caliper measurement is positioned on the selected frame.

15. The system of claim 9, comprising one or both of:
an ultrasound probe configured to provide the at least one processor with the multi-frame two-dimensional image of the region of interest, and
an archive configured to provide the at least one processor with the multi-frame two-dimensional image of the region of interest.

16. A non-transitory computer readable medium having stored thereon, a computer program having at least one code section, the at least one code section being executable by a machine for causing the machine to perform steps comprising:
selecting a frame of a multi-frame two-dimensional image of a region of interest;
positioning a first caliper measurement on the selected frame;
generating an anatomical motion mode image based on a direction of the first caliper measurement;
automatically overlaying a second caliper measurement on the anatomical motion mode image, the second caliper measurement corresponding with the first caliper measurement on the selected frame; and
presenting the selected frame having the first caliper measurement simultaneously with the anatomical motion mode image having the second caliper measurement at a display system.

17. The non-transitory computer readable medium of claim 16, comprising receiving at least one measurement selection, wherein the frame is automatically selected based on the at least one measurement selection.

18. The non-transitory computer readable medium of claim 16, comprising receiving at least one measurement selection, wherein the first caliper measurement is automatically positioned on the selected frame by processing the selected frame to locate anatomical landmark points corresponding to measurement end points defined by the at least one measurement selection, and wherein the anatomical landmark points are automatically located based on machine-learning algorithms.

19. The non-transitory computer readable medium of claim 16, comprising:
automatically processing the anatomical motion mode image and coordinates of the first caliper measurement based on machine-learning algorithms to determine whether the selected frame is a correct frame; and
adjusting the first caliper measurement if the selected frame is not the correct frame by:
selecting a new frame of the multi-frame two-dimensional image of the region of interest based on temporal information of the anatomical motion mode image, and
positioning the first caliper measurement on the selected new frame.

20. The non-transitory computer readable medium of claim 16, wherein the anatomical motion mode image having the second caliper measurement is presented at the display system at substantially a same time as the first caliper measurement is positioned on the selected frame.

* * * * *